US012685480B2

(12) United States Patent
Fernandez Rivas et al.

(10) Patent No.: US 12,685,480 B2
(45) Date of Patent: Jul. 21, 2026

(54) MATERIAL CHARACTERIZATION METHOD

(71) Applicant: Universiteit Twente, Enschede (NL)

(72) Inventors: David Fernandez Rivas, Enschede (NL); Miguel Angel Quetzeri Santiago, Enschede (NL)

(73) Assignee: Universiteit Twente, Enschede (NL)

( * ) Notice: Subject to any disclaimer, the term of this patent is extended or adjusted under 35 U.S.C. 154(b) by 0 days.

(21) Appl. No.: 18/836,911

(22) PCT Filed: Feb. 10, 2023

(86) PCT No.: PCT/NL2023/050058
§ 371 (c)(1),
(2) Date: Aug. 8, 2024

(87) PCT Pub. No.: WO2023/153926
PCT Pub. Date: Aug. 17, 2023

(65) Prior Publication Data
US 2025/0143630 A1     May 8, 2025

(30) Foreign Application Priority Data
Feb. 11, 2022     (NL) ...................................... 2030901

(51) Int. Cl.
*A61B 5/00* (2006.01)
*A61F 9/00* (2006.01)
*A61M 5/30* (2006.01)

(52) U.S. Cl.
CPC ............ *A61B 5/442* (2013.01); *A61B 5/0053* (2013.01); *A61F 9/0008* (2013.01); *A61M 5/30* (2013.01)

(58) Field of Classification Search
None
See application file for complete search history.

(56) References Cited

U.S. PATENT DOCUMENTS

2010/0004624 A1* 1/2010 Hunter ................... A61B 5/442
604/503
2011/0319791 A1 12/2011 Harry et al.

FOREIGN PATENT DOCUMENTS

| FR | 3006448 A1 * | 12/2014 | ............ G01N 29/09 |
|---|---|---|---|
| WO | 2008142640 A1 | 11/2008 | |
| WO | 2010150154 A1 | 12/2010 | |
| WO | 2020182665 A1 | 9/2020 | |

OTHER PUBLICATIONS

International Search Report and Written Opinion, PCT Application No. PCT/NL2023/050058, mailed Mar. 28, 2023 (10 pages).

* cited by examiner

*Primary Examiner* — Yi-Shan Yang
(74) *Attorney, Agent, or Firm* — J. Robin Rohlicek

(57) ABSTRACT

The invention provides a method for determining a property of a target area of a material, wherein the target area has a size selected from the range of 100 $\mu m^2$-100 $mm^2$, wherein the method comprises: an exposure stage comprising providing a liquid jet to the target area, wherein the liquid jet has a jet velocity selected from the range of 2-150 m/s; a measurement stage comprising detecting a deformation of the material in the target area and providing a related signal; and an analysis stage comprising determining the property of the target area based on the related signal.

25 Claims, 6 Drawing Sheets

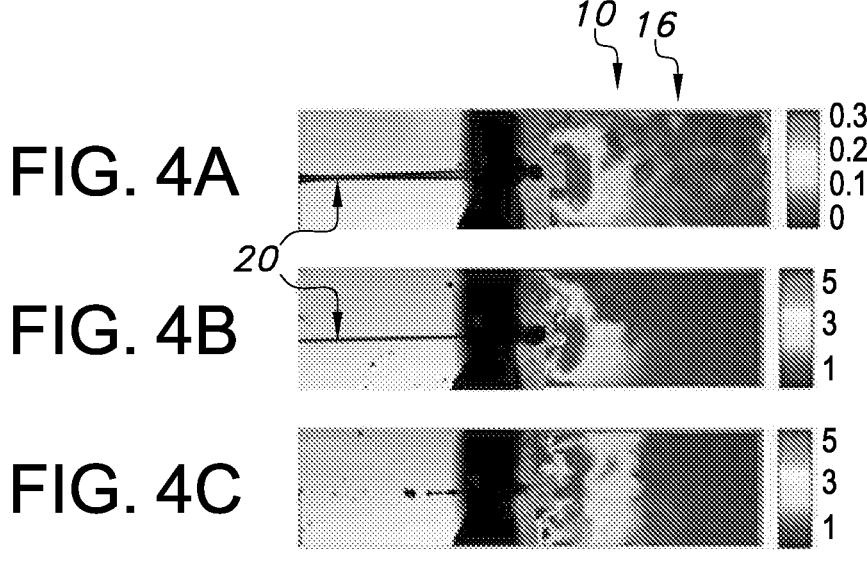
FIG. 4A
FIG. 4B
FIG. 4C
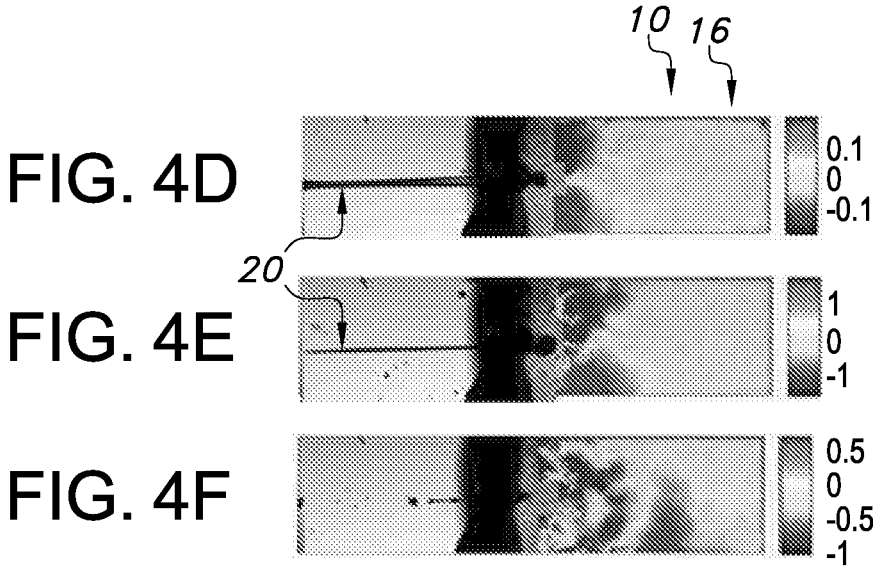
FIG. 4D
FIG. 4E
FIG. 4F

MATERIAL CHARACTERIZATION METHOD

CROSS REFERENCE TO RELATED APPLICATIONS

This application is a national phase under 35 CFR 371 of international application no. PCT/NL2023/050058, filed Feb. 10, 2023, which claims the benefit of the priority filing date of Netherlands application no. 2030901, filed Feb. 11, 2022, the contents of all of which are hereby incorporated by reference in their entireties.

FIELD OF THE INVENTION

The invention relates to a method for determining a property of a target area of a material. The invention further relates to an injection method for injecting a fluid into a material. The invention further relates to a system for determining a property of a target area of a material.

BACKGROUND OF THE INVENTION

Methods for measuring a property of a material are known in the art. For instance, US2006052719A1 describes a method of determining skin anisotropy of a subject by measuring rates of propagation of mechanical energy between a mechanical energy generator and a mechanical energy detector along a plurality of directions of an expanse of skin wherein each of the directions are from about 0° to about 10° in separation relative at least one other of the directions and at least two of the directions are from about 30° to about 180° in separation relative to each other.

FR3006448A1 describes an ultrasonic device and method for measuring, inspecting and classifying the mechanical and/or thermal properties of a medium, by means of at least one broadband source of acoustic waves coupled to at least one solid guide with elastic waves of known impedance and effusivity, housed and damped in an insulating structure acoustically and thermally and coupled with the medium on a determined surface with a controlled bearing force, said coupling being able to result from a first coupling of the solid guide to a continuously projected liquid guide with a constant or variable hydrostatic pressure, said liquid also being able to be heated and projected intermittently, in the form of a collimated jet striking the surface of the medium.

WO2010150154A1 describes a device for detecting a temporal alteration of an optical property of a subcutaneous layer in vivo, drug delivery device comprising the arrangement and method for drug delivery are described. For an optimized control of drug delivery by a transdermal drug delivery device an optical feedback control is described, which allows to detect the alteration of an optical property of a subcutaneous layer caused by an injected fluid from a fluid jet.

US2011319791A1, "Systems and Methods for Measuring Mechanical Properties of Deformable Materials", (D3) describes a system to deform the surface of the material with a probe, such as a mechanical device or a gas/liquid jet, while optically recording the three-dimensional (3D) topography of the resulting surface deformation.

SUMMARY OF THE INVENTION

The properties of viscoelastic materials, such as skin, reported in the literature may vary greatly, both due to the large number of methods used, as well as due to the heterogeneous and/or multi-layer nature of (some) viscoelastic materials, such as of skin. For example, skin fracture may depend on parameters such as relative humidity, temperature, age, and how the force or load is applied (static or dynamic). The resulting skin critical stress values, $\sigma_{crit}$, can be found with a wide range 500 kPa-20 MPa for static loading. Besides critical stress, the measurement of other mechanical properties may be strongly influenced by the type of probe used, e.g., indentometers may give different values dependent on the size of the indenter, and the dynamics of the applied load. In particular, measuring skin properties under realistic conditions, ex vivo or in vivo, may be challenging.

For instance, accurate measurements of a property of skin may facilitate needle-free jet injections into the skin as characteristics of the needle-free jet injection may be tuned accordingly. Thereby, a desired dose of a medicament may be accurately provided to a desired injection depth. For example, insulin may typically be tailored for delivery in the subcutaneous fat due to consistent perfusion, but its uptake may be better in the dermis. Similarly, vaccines targeting antigen presenting cells may beneficially be delivered into the dermis, but targeting this thin layer with consistency may be challenging. Similarly, nucleic acid (DNA) or ribonucleic acid (RNA) vaccines, such as those created to treat Covid-19, may benefit from delivery into the dermis.

In contrast, when a jet injection takes place with unsuitable energy settings, such as due to an incorrect measurement or assumption of an in situ skin property, the injected liquid may potentially be injected too shallowly or too deeply, i.e., it may inadvertently reach an unintended skin layer. For instance, if a liquid jet is provided with insufficient power the jet may not penetrate the skin and rejected liquid may splash back, which may lead to the delivery of a wrong dose of a medicament, may risk contaminating the injector parts, and may inadvertently contact a healthcare giver's body. Further, if a liquid jet is provided with excess power bruising may occur, which may be painful and aesthetically undesirable.

Further, skin is anisotropic, i.e., a physical property of skin may vary dependent on how it's measured, such as locally or on a larger scale. The term "anisotropic" with respect to a material may refer to the heterogenous response of the material upon a stimulus, i.e., the material will respond differently to the stimulus in different directions.

Further, properties of viscoelastic materials, such as skin, may be rate dependent, meaning that the material may respond differently depending on the duration and timescale of a stimulus.

As, for instance, jet injection may be relatively local, it may be desirable to determine the relevant skin parameters locally.

The prior art may describe methods for measuring a property of a material, such as of skin, by statically deforming the material with multiple traction surfaces to determine strain. The contact with the material can cause irreversible deformations, like damage, such as bruising with respect to a skin, and potentially also contamination. Additionally, the timescale of the deformation may not provide a suitable estimation of the material property at the rates for needle-free injection. Further, with respect to skin, such deformation may induce discomfort on the subject.

The prior art may further describe methods for measuring a property of a material by introducing vibrations to the skin with a mechanical shaker, and determining a property based on a detected surface wave. However, the measurement of the property may not be made locally, but may rather be averaged on a large part of the material. Therefore, it could lead to inaccurate local measurements. Also, contact with the material may lead to contamination.

Prior art methods may further have a relatively low frequency range for deformation of the skin. However, the determined material properties may not extend to "fast" deformations give the typical rate-dependency of properties of viscoelastic materials, such as would be relevant for a needle-free injection. Further, slow measurement rates may be more sensitive to errors caused by changing properties of a material as a function of, for instance, humidity and stress.

Further, prior art methods may require a large number of measurements to determine the value of a property of the material, such as skin, in different directions.

Yet further, prior art methods may (locally) induce irreversible changes like damage the material.

Similarly, also for other viscoelastic materials, such as coatings, it may be desirable to measure their (viscoelastic/mechanical) properties in a controlled, local and/or non-invasive manner.

Hence, it is an aspect of the invention to provide an alternative method for determining a property of a target area of a material, which method preferably further at least partly obviates one or more of above-described drawbacks. The present invention may have as object to overcome or ameliorate at least one of the disadvantages of the prior art, or to provide a useful alternative.

Hence, in a first aspect, the invention may provide a (characterization) method for determining a property of a target area of a (viscoelastic) material. In embodiments, the target area may have a size selected from the range of 100 $\mu m^2$-100 $mm^2$. The method may comprise one or more of an exposure stage, a measurement stage, and an analysis stage. The exposure stage may especially comprise providing a liquid jet to the target area, especially wherein the liquid jet has a jet velocity selected from the range of 2-150 m/s. The measurement stage may comprise detecting a (spatiotemporal) deformation of the material in the target area, and especially providing a related signal. The analysis stage may comprise determining the property of the target area based on the detected deformation, especially based on the related signal.

The method of the invention may provide the benefits that the material can be deformed locally, non-invasively, at a high frequency, and efficiently in time. For instance, by jetting continuously or using a train of droplets have a frequency range of 0.001-50 kHz may be covered. The measurements may be (essentially) continuous with a spatial resolution <10 $\mu m$, such as <5 $\mu m$. The method may further facilitate determining various properties of the material, such as strain, Young's modulus, viscous modulus, shear elasticity, and shear viscosity. Further, the method may facilitate determining the anisotropy in multiple directions with a single measurement. Further, the method may simultaneously probe the material and provide a liquid, especially comprising an additive (see below) to the material, such as to prepare the material for a subsequent injection.

The invention may herein for explanatory purposes be primarily discussed in the context of measuring a property of skin. It will be clear to the person skilled in the art, however, that the invention is not limited to such embodiments and may, for instance, also apply to measuring a property of a coating.

Hence, in specific embodiments, the invention may provide a method for determining a property of a target area of a material, wherein the target area has a size selected from the range of 100 $\mu m^2$-100 $mm^2$, wherein the method comprises: an exposure stage comprising providing a liquid jet to the target area, wherein the liquid jet has a jet velocity selected from the range of 2-150 m/s; a measurement stage comprising detecting a deformation of the material in the target area and providing a related signal; and an analysis stage comprising determining the property of the target area based on the related signal. Hence, the invention may provide a (characterization) method for determining a property of a target area of a material.

In embodiments, the property may especially comprise a dynamic property. In further embodiments, the property may especially comprise a mechanical property (or "viscoelastic property"). In further embodiments, the property may be selected from the group comprising a Young's modulus, a viscous modulus, a shear elasticity, and a shear viscosity. The term "property" may herein also refer to a plurality of (different) properties, such as to both a Young's modulus and a viscous modulus.

The material may especially be a viscoelastic material, i.e., a material that exhibits both elastic and viscous behavior when deformed. For instance, in embodiments, the material may comprise a polymer. In further embodiments, the material may comprise (ex vivo) soft tissue, such as (ex vivo) skin, or such as an (ex vivo) eye. In further embodiments, the material may comprise a hydrogel, such as one or more of gelatin, agarose and a polyacrylamide. Gelatin and agarose may be commonly used to give texture to foods and also as skin surrogates. Polyacrylamide may, for instance, be used for studies on cell durotaxis (the ability of cells to move in a substrate with a stiffness gradient). In further embodiments, the material may comprise an artificially created tissue or a biomaterial, such as a dermal equivalent or a cell cultivation tissue for an implant, for example 3D printed tissues and organs.

The term "target area" may herein especially refer to an area of the material of which the property is determined, i.e., the property may be specifically determined for the target area. In particular, (part of) the target area may also be exposed to the liquid jet (see below). In embodiments, the target area may have a size selected from the range of 50 $\mu m^2$-150 $mm^2$, especially from the range of 100 $\mu m^2$-100 $mm^2$, such as from the range of 200 $\mu m^2$-30 $mm^2$. In further embodiments, the target area may especially have a size from the range of 300 $\mu m^2$-3 $mm^2$, such as from the range of 500 $\mu m^2$-1 $mm^2$. In further embodiments, the target area may especially have a size selected from the range of 100 $\mu m^2$-1 $mm^2$.

The method may especially comprise one or more of an exposure stage, a measurement stage, and an analysis stage. In particular, in embodiments, the method comprises the exposure stage, the measurement stage, and the analysis stage.

In embodiments, the method may comprise the exposure stage. The exposure stage may comprise providing a liquid jet (or "jet") to the target area. In particular, the exposure stage may comprise ejecting a liquid jet, such as with a jet ejection system, towards the target area such that the liquid jet impacts on the target area.

In general, the term "jet" may refer to a natural or man-made collimated stream of matter. For example, generating a jet (also: "jetting") may be possible from small orifices or nozzles. Herein, the term "jet" refers to a high-velocity and low-diameter stream of liquid forced out of a (small) opening. A jet may have a velocity of at least 1 m/s. In embodiments, the jet may have a high stability i.e., the jet may essentially comprise a substantially continuous, especially unbroken, liquid stream. In further embodiments, the jet may comprise a stream of successive individual droplets.

The jet may have a (jet) diameter selected from the range of 10-3000 μm, such as from the range of 15-500 μm, especially selected from the range of 25-300 μm, such as selected from the range of 50-150 μm. Hence, in embodiments, the individual droplets (of the stream of successive individual droplets) may (each) have a diameter selected from the range of 10-3000 μm, such as from the range of 15-500 μm, especially selected from the range of 25-300 μm, such as selected from the range of 50-150 μm.

Jet ejection systems and methods are known in the art. For instance, the method of the invention may be performed by ejecting a liquid jet on the target area with the system described in WO2020182665, which is hereby herein incorporated by reference.

In embodiments, the exposure stage may comprise providing the liquid jet with a jet velocity selected from the range of 1-250 m/s, such as from the range of 2-150 m/s, especially from the range of 5-70 m/s. The jet velocity may especially be selected in view of the material, such as in view of (typical) properties of such a material. In particular, the jet velocity may be selected to be sufficiently high to provide an (observable) deformation in the material (by a sensor system). Further, the jet velocity may be selected to be sufficiently low not to damage, such as rupture, the material. It will be clear to the person skilled in the art that the jet velocities suitable for providing an (observable) deformation without (substantially) damaging the material will depend on not only the material, but also on other jet properties of the liquid jet, such as jet diameter, jet volume and/or jet angle (to the target area). The jet velocity may especially be selected to be sufficient to provide a deformation of the target area, such as based on the material. The jet velocity may further be selected to be below an (estimated) threshold for injection into the material. Generally, the jet velocity of the liquid jet may be (relatively) stable from the moment of ejection to the moment of impact on the target site. The jet velocities mentioned herein may, however, especially refer to the jet velocity of the liquid jet right before impact of the liquid jet on the target area. Hence, in embodiments, the jet velocity may be the jet velocity upon (or "right before") impact of the liquid jet on the target area. In further embodiments, the jet velocity may be the jet velocity upon generation of the jet, such as the jet velocity of the liquid jet as the liquid jet leaves a microfluidic device.

In further embodiments, the exposure stage may comprise providing the liquid jet to the target area from a distance ≤50 cm, such as ≤20 cm, especially ≤10 cm. In further embodiments, the exposure stage may comprise providing the liquid jet to the target area from a distance ≤5 cm, especially ≤3, such as ≤2 cm (relative from a position at the microfluidic device where the liquid jet leaves the microfluidic device). In further embodiments, the exposure stage may comprise providing the liquid just to the target area from a distance ≥1 cm, such as ≥3 cm, especially ≥5 cm.

In further embodiments, the exposure stage may comprise providing the liquid jet with a jet volume selected from the range of ≤500 μL, such as ≤200 L, especially ≤100 μL. In further embodiments, the exposure stage may comprise providing the liquid jet with a jet volume selected from the range of ≤10 μL, such as ≤5 μL, especially ≤1 μL. In further embodiments, the exposure stage may comprise providing the liquid jet with a jet volume selected from the range of ≤500 nL, such as ≤300 nL, especially ≤100 nL.

In further embodiments, the exposure stage may comprise providing the liquid jet with a jet volume selected from the range of 2-50 nL, such as from the range of 5-25 nL, especially from the range of 8-13 nL. In particular, a (relatively) low jet volume may be selected to avoid a pooling of liquid on the target area, which may obscure the measuring of a deformation. Hence, in further embodiments, the exposure stage may comprise providing the liquid jet with a jet volume selected from the range of ≤75 nL, such as ≤50 nL, especially ≤40 nL. In further embodiments, the exposure stage may comprise providing the liquid jet with a jet volume selected from the range of ≤30 nL, such as ≤20 nL, especially ≤15 nL.

In further embodiments, the jet volume may be selected from the range of ≥1 nL, such as ≥2 nL, especially ≥5 nL. In further embodiments, the jet volume may be selected from the range of ≥10 nL, especially ≥20 nL, such as ≥50 nL, especially ≥100 nL. In further embodiments, the jet volume may be ≥1 μL, such as ≥5 μL, especially ≥10 μL, such as ≥100 μL.

In further embodiments, the exposure stage may comprise providing the liquid jet with a circular equivalent (jet) diameter selected from the range of 20 μm-5 mm, such as from the range of 30 μm-3 mm, especially from the range of 50 μm-1 mm. In particular, a small circularly equivalent diameter may facilitate a more local detection of the property. Hence, in embodiments, the circular equivalent diameter may especially be ≤3 mm, such as ≤1 mm, especially ≤500 μm, such as ≤100 μm.

The equivalent circular diameter (or ECD) (or "circular equivalent diameter") of an (irregularly shaped) two-dimensional shape is the diameter of a circle of equivalent area. For instance, the equivalent circular diameter of a square with side a is $2*a*SQRT(1/\pi)$. For a circle, the diameter is the same as the equivalent circular diameter. Would a circle in an xy-plane with a diameter D be distorted to any other shape (in the xy-plane), without changing the area size, then the equivalent circular diameter of that shape would be D. In particular, the circular equivalent diameter of the liquid jet may be determined in a plane perpendicular to a travel path of the liquid jet (towards the target area).

In further embodiments, the liquid jet may have a circularly equivalent (jet) diameter D2, and the target area may have a circularly equivalent (target) diameter D3, wherein D3 is selected from the range of 3*D2-30*D2, such as from the range of 5*D2-20*D2, especially from the range of 7*D2-15*D2.

In further embodiments, the exposure stage may comprise providing the liquid jet with a spherical equivalent (jet) diameter selected from the range of 30 μm-3 mm.

The equivalent spherical diameter (or ESD) (or "spherical equivalent diameter") of an (irregularly shaped) three-dimensional shape is the diameter of a sphere of equivalent volume. For a sphere, the diameter is the same as the equivalent spherical diameter. Would a sphere in an xyz-plane with a diameter D be distorted to any other shape (in the xyz-plane), without changing the volume, then the equivalent spherical diameter of that shape would be D.

In general, the liquid jet may be provided perpendicularly to the target area, i.e., the liquid jet may travel along a path (essentially) perpendicularly to the target area before impacting on the target area. Providing the liquid jet (essentially) perpendicularly to the target area may provide the benefit that an (essentially) uniform force may be provided in in-plane directions of the target area, which may facilitate determining the property in different directions as the ensuing deformation may differ in different directions from the impact site. Hence, in embodiments, the exposure stage may comprise providing the liquid jet to the target area at an (jet) angle of 45°-90° (to the target area), such as at an angle of 60-90°, especially at an angle of 75-90°, such as at an angle of 85-90°, especially (essentially) 90°.

However, in embodiments, the liquid jet may also be provided at an angle (relative to the perpendicular) to the target area. Providing the liquid jet at an angle may provide the benefit that the liquid jet is less likely to penetrate the material, and may provide a (radially) asymmetric response of the material to the impact of the liquid jet, which may provide additional information. In particular, the property of the material may be probed in a shear-dependent regime. Further, providing the liquid jet at an angle may facilitate measuring at an area that is uneven.

Hence, in embodiments, the exposure stage may comprise providing the liquid jet to the target area at an angle of 30°-85° (to the target area), such as at an angle of 45-80°, especially at an angle of 50-75°.

As described above, the material may be anisotropic, i.e., the (value of the) property of the material may depend on the measurement conditions. Hence, in embodiments, the exposure stage may comprise varying the measurement conditions (over time). Thereby, the property may be conveniently determined with respect to a variety of measurement conditions, which may also facilitate inter- or extrapolating the (value of the) property to non-measured conditions.

Hence, in embodiments, the exposure stage may comprise varying a jet property of the liquid jet (over time). For instance, the exposure stage may comprise varying the (circularly or spherically equivalent) diameter or jet velocity of the liquid jet over time. In particular, in embodiments, the exposure stage may comprise varying one or more of the jet velocity, the (circular or spherical equivalent) diameter, and the jet angle (relative to the target area) of the liquid jet. For instance, varying the jet (impact) velocity in time could inform on the dependence of the material property with the impact force. Further, for example, varying the frequency at which the liquid jet, especially the plurality of droplets, are provided may inform on the dependence of the material property with respect to the strain rate. Varying the jet diameter may especially refer to varying one or more of the circular equivalent diameter of the liquid jet and the spherical equivalent diameter of the liquid jet, especially the circular equivalent diameter of the liquid jet.

In further embodiments, the exposure stage may comprise varying the jet velocity, especially in the range of 1-250 m/s, such as in the range of 2-150 m/s, especially in the range of 5-70 m/s.

In further embodiments, the exposure stage may comprise varying the jet circular (or spherical) equivalent diameter of the liquid jet in the range of 10 μm-5 mm, especially in the range of 20 μm-4 mm, such in the range of 30 μm-3 mm.

In further embodiments, the exposure stage may comprise varying the jet angle, especially in the range of 45°-90° (to the target area).

As described above, the method may further comprise providing a plurality of (successively provided) droplets to the target area. In particular, in embodiments, the exposure stage may comprise providing the liquid jet, wherein the liquid jet comprises a plurality of (successively provided) droplets. Especially, (droplets in) the plurality of droplets may be provided at intervals (independently) selected from the range of 0.02-10 ms, such as selected from the range of 0.05-5 ms, especially from the range of 0.1-2 ms.

Hence, in embodiments, the exposure stage may comprise providing the plurality of droplets at a frequency selected from the range of 0.001-50 kHz, such as from the range of 0.1-50 kHz, especially from the range of 1-30 KHz.

In particular, in embodiments, the exposure stage may comprise varying the properties of two or more of the plurality of droplets, such as by continuously, especially linearly, changing a property of the droplets, or such as by step-wise changing a property of the droplets (e.g., 5 droplets with (essentially) a first set of properties followed by 5 droplets with a second set of properties).

Hence, in embodiments, the exposure stage may comprise varying a jet property of the liquid jet (over time) by varying the jet property along the plurality of (successively provided) droplets.

In further embodiments, the exposure stage may comprise varying the intervals between two or more successive droplets of the plurality of droplets, i.e., two or more successive intervals may differ in duration. Especially, the exposure stage may comprise varying the frequency at which the plurality of droplets are provided (over time). In particular, in embodiments, the exposure stage may comprise varying the frequency in the range of 0.1-50 kHz.

In further embodiments, the exposure stage may comprise providing a frequency sweep, such as in the range of 0.001-50 kHz, such as in the range of 0.1-50 kHz, especially in the range of 1-30 kHz. The term "frequency sweep" may herein especially refer to starting at a first frequency and continuously or step-wise adjusting the frequency until a terminal frequency, and optionally (continuously or step-wise) reverting to the starting frequency. Thereby, the response of the material to different impact frequencies may be determined in an efficient manner.

As indicated above, the changing of a jet property in the exposure stage may occur in a step-wise manner. In particular, in embodiments, the exposure stage may comprise a first phase and a second phase, wherein the first phase and the second phase differ in one or more of jet velocity, jet intervals, jet angle, and jet diameter. In further embodiments, the first phase and the second phase may differ (at least) in jet velocity. In further embodiments, the first phase and the second phase may differ (at least) in jet intervals. In further embodiments, the first phase and the second phase may differ (at least) in jet angle. In further embodiments, the first phase and the second phase may differ (at least) in jet diameter.

The method may further, in embodiments, comprise the measurement stage. The measurement stage may comprise detecting a (spatiotemporal) deformation of the (viscoelastic) material in the target area, and especially to provide a related signal. For instance, in embodiments, the measurement stage may comprise detecting radiation, such as optical or acoustic radiation, from the target area. As the target area may deform due to the impact of the jet and the deformation may affect the reflection of radiation, the detected radiation may be indicative of the deformation.

The term "related signal" may herein refer to a signal that is related to the detected deformation. In particular, the related signal may comprise raw and/or processed data related to the (detected) deformation.

In embodiments, the measurement stage may comprise projecting a mark on (at least part of) the target area, such as with (optical) radiation. For instance, the mark may comprise a (straight) line or a pattern, such as a (regular) 2D grid or planar light, especially a (regular) 2D grid. As the deformation of the target area due to the impact of a liquid jet may comprise an indentation and/or a surface wave, the mark may undergo a mark deformation as a result of the changing (relative) height of the area projected on. For instance, such as when the mark comprises a (regular) 2D grid, the mark may resemble a mesh surface plot, which may facilitate determining and quantifying the deformation.

In further embodiments, the measurement stage may especially comprise optically detecting the deformation in the target area, such as by detecting optical (measurement) radiation from the target area, especially including detecting a mark deformation in the mark.

In further embodiments, the measurement stage may comprise acoustically detecting the deformation in the target area, such as by detecting acoustic (measurement) radiation from the target area.

The (measurement) radiation may be ambient radiation, such as provided by an ambient light source, but may also be specifically to facilitate measuring. In particular, providing the (measurement) radiation to the target area and detecting (reflected) radiation may result in reduced measurement noise and/or uncertainty.

Hence, in embodiments, the measurement stage may comprise (i) providing (measurement) radiation, especially laser radiation, to the target area, and (ii) detecting reflected (measurement) radiation from the target area, and especially providing a related signal. In embodiments, the radiation may comprise optical radiation. In further embodiments, the radiation may comprise acoustic radiation. Hence, in embodiments, the related signal may be based on the detected reflected radiation, such as comprise raw and/or processed data based on the detected reflected radiation.

As described above, the impact of the liquid jet on the target area of the material may result in a surface wave travelling along a surface of the material. In particular, the surface wave may be informative with regards to the (viscoelastic) property of the material. Hence, in embodiments, the measurement stage may comprise measuring a wave property of a surface wave (following impact of the liquid jet on the material) in the target area, especially wherein the wave property is selected from the group comprising a propagation velocity and an amplitude decay, and especially providing a related signal.

In embodiments, the method may especially comprise measuring the deformation using a sensor (array). In further embodiments, the method may comprise measuring the deformation using laser profilometry, i.e., directing a laser line to a surface such that it is reflected to a (high speed) camera. When the surface is deformed, then the laser line deviates and both the amplitude of the wave and the wave speed can be measured. With laser profilometry, the wave amplitude can be measured with a precision <40 μm.

In embodiments, the method may further comprise an analysis stage. The analysis stage may comprise determining the (viscoelastic) property of the target area based on the (detected) deformation, especially based on the related signal. In further embodiments, the analysis stage may comprise determining the property of the target area based on the (detected) reflected (measurement) radiation. In further embodiments, the analysis stage may comprise determining the property of the target area based on the wave property.

For instance, the analysis stage may comprise determining a (viscoelastic) property of the target area based on propagation of a surface wave. Properties of the surface wave such as the velocity of propagation and the amplitude decay over the surface of the material may be introduced into a model to determine the Young's modulus of the material and the viscous modulus $\beta$. Assuming that the material is isotropic along a single radial direction and viscoelastic a relationship between the surface wave speed $c_s$ is related to the Young's modulus E of the skin by:

$$c_s = \frac{1}{1.05}\sqrt{\frac{E}{3\rho}}$$

where $\rho$ is the density of the material.

The wave decay rate due to viscosity can be calculated from wave amplitudes acquired at two different locations of the skin with the relation:

$$\gamma = -\frac{\log\left(\frac{z(r_2)\sqrt{r_2}}{z(r_1)\sqrt{r_1}}\right)}{r_2 - r_1}$$

where $z(r_1)$ and $z(r_2)$ are the wave amplitudes at the locations $r_1$ and $r_2$ respectively, $r_2$-$r_1$ is the distance between $r_1$ and $r_2$, and $\gamma$ is the decay rate due to viscosity. Next, the complex modulus E* of the material may be determined with:

$$E^* = E(1 + i\beta)$$

where $$\beta = \frac{2\gamma c_s}{\omega},$$

where $i=\sqrt{-1}$, and wherein $\omega$ is the angular wave frequency.

Similarly, as the shear viscosity u may relate to the Young's modulus E, the shear viscosity $\mu$ may also be determined using the method of the invention, such as based on a predetermined relationship between the shear viscosity $\mu m$ and the Young's modulus E. For instance, with respect to agarose gels, the shear viscosity may be (approximately) determined according to:

$$\mu = 6.005 * 10^{-5}E + 0.00834$$

In further embodiments, the property may comprise the fracture point, the yielding point, the toughness and the Poisson's ratio of the target area.

In particular, the fracture point (or "breaking point") may be defined as the point where a material breaks upon application of stress. The fracture point may be measured by observing penetration of the target area by the liquid jet.

The yielding point can be measured by gradually increasing impact velocities up to a point where the material gets permanently deformed. Specifically, For finding the yielding point the jet (impact) velocity (representing stress) may be increased gradually. Before the impact and at each jet velocity the depth at several positions can be measured $z(r\_n)$. The yielding point would be reached for the impact velocity at which at least one $z(r\_n)$ does not return to the original position.

The toughness of the material may be associated with the yielding point. In particular, the toughness may be the area under the stress-strain curve, until the fracture point. The strain can be obtained by measuring the displacements at each time of $z(r\_n)$ (close to the impact point).

Poisson's ratio can be measured by measuring the depth and width of the material deformation upon impact. Specifically, Poisson's ratio may be determined based on the aspect ratio of the deformation profile formed during impact, i.e., by taking the ratio between $z\_max$ ($r\_0$) and $r\_max$, where $r\_0$ is the center of the impact and wherein $z\_max$ is the maximum depth of the deformation and $r\_max$ is the maximum radius of the deformation.

In addition, if a plurality of droplets is provided to the target area at a given frequency, and keeping the frequency, the jet velocity is increased, at the fracture point, the modes of oscillation of the material may change. The change from before fracture (under vibration) and after fracture (during vibration) may indicate the fracture point, i.e., a fracture (or "break") in the material may be observed via a change in a wave propagation signal.

The term "stage" and similar terms used herein may refer to a (time) period (also "phase") of a method and/or an operational mode. The different stages may (partially) overlap (in time). For example, the measurement stage may, in general, be initiated prior to the exposure stage and may extend past the exposure stage. However, for example, the measurement stage may typically be completed prior to the analysis stage. It will be clear to the person skilled in the art how the stages may be beneficially arranged in time. For example, the measurement stage may be initiated prior to the exposure stage to measure the target area prior to deforming, such that the deformation can be accurately determined.

In embodiments, the method may further comprise a preparation stage. The preparation stage may comprise providing an additive to the target area, especially wherein the additive comprises one or more of water and oil. For instance, the method may comprise providing a preparation jet to provide the additive to the target area. In further embodiments, the additive may comprise a liquid or a semisolid, such as a gel or a crème. In particular, the additive may be provided for one or more of (i) homogenizing the target area, (ii) facilitating measuring, (iii) enhancing the penetration by needle-free injection systems, (iv) (pre-) tensioning the material, and (v) providing more reproducible properties, such as by saturating the material with water. For instance, for a (relatively) smooth material, it may be relatively challenging to detect a deformation. Hence, an additive comprising visible particles may be provided to the target area (or a 2D grid may be projected on the target area), such that deformation-related movement of the visible particles may be detected for (part of) measuring the deformation.

In embodiments, the additive may comprise a penetration enhancer, such as to facilitate a subsequent injection during an injection stage. Especially, the additive may comprise a penetration enhancer selected from the group comprising ethanol, dimethyl sulfoxide, sodium dodecyl sulphate and propylene glycol.

Further, an additive may be provided to the target area of the material in order to determine the effects of the additive on a (viscoelastic) property of the additive on the material, such as to determine the effect of a moisturizing cream on a property of skin.

In further embodiments, the preparation stage may comprise ablation of (at least part of) the target area. Similarly, to providing an additive, ablation may facilitate homogenization of the target area prior to measuring.

In further embodiments, in the exposure stage, the liquid jet may comprise the additive, especially wherein the additive comprises a penetration enhancer.

In embodiments, the method, especially the exposure stage, may comprise controlling one or more of a temperature, a tension, and a humidity of the target area. The method may, for instance, comprise providing a tension to the target area, such as via a contact element (see below). Similarly, to described above for the jet property, the temperature, tension and humidity the material is exposed to may affect the property of the material. Hence, the method may comprise measuring the property under controlled conditions, or may comprise varying one or more of the temperature, tension and humidity to determine the property under a variety of conditions, which may further facilitate inter- and extrapolating the property for, for instance, other temperatures.

In embodiments, the material may comprise (animal) skin, especially ex vivo skin, or especially in vivo skin. In further embodiments, the material may comprise human skin. For instance, the method may comprise determining a property of the skin, such as to facilitate future jet injection (see below).

In further embodiments, the method may be a non-medical method, especially a non-diagnostic method.

In further embodiments, the material may comprise an inanimate material. For instance, in embodiments, the material may comprise a coating.

In a second aspect, the invention may provide an injection method for injecting a fluid in a material. The injection method may especially comprise one or more of a characterization stage, a parameterization stage and an injection stage. The characterization stage may especially comprise determining a (viscoelastic) property of a target area of the material with the (characterization) method of the invention. The parameterization stage may comprise selecting a (value of a) second jet property for injecting the fluid into the material based on the (determined) property (of the material), wherein the second jet property is selected from the group comprising a jet velocity, a jet volume, a jet (ejection) rate, and a jet angle. The injection stage may comprise ejecting a second liquid jet towards (the target area of) the material based on the (value of the) second jet property, wherein the second liquid jet comprises the fluid, and especially wherein the second liquid jet has the (value of the) jet property.

The injection method of the invention may thus beneficially (i) determine a (viscoelastic) property of a target area of the material using a (first) liquid jet based on the (characterization) method of the invention, (ii) select an appropriate second jet property for injecting into the material based on the (viscoelastic) property, and (iii) provide a second liquid jet having the second jet property to the target area. Thereby, the injection method may tune the properties of the second liquid jet to the local properties of the target area of the material, in order to improve jet injection, such as by providing an improved accuracy in injection volume and/or injection depth.

Hence, in embodiments, the parameterization stage may comprise selecting a second jet property for injecting the fluid into the (target area of the) material based on the (viscoelastic) property. The second jet property may especially be selected from the group comprising a jet velocity, a jet volume, a jet (ejection) rate, such as a jet (ejection) frequency, and a jet angle (with respect to the target area). The term "second jet property" may herein also refer to a plurality of second jet properties. Hence, in embodiments, the second jet property may (at least) comprise the jet velocity. In further embodiments, the second jet property may (at least) comprise the jet volume. In further embodiments, the second jet property may (at least) comprise the jet rate. In further embodiments, the second jet property may (at least) comprise the jet angle.

In particular, in embodiments, the parameterization stage may comprise selecting the second jet property based on the (viscoelastic) property and a target parameter, especially wherein the target parameter is selected from the group comprising an injection depth and an injection volume.

In further embodiments, the injection stage may comprise ejecting a second liquid jet towards the material based on the second jet property, especially towards the target area of the material. Especially, the second liquid jet may have the second jet property. Further, the second liquid jet may especially comprise the fluid. For example, the fluid may comprise a compound selected from the group comprising insulin, painkillers, vaccines, and biosensor molecules. In further embodiments, the fluid may be selected from the group comprising surfactants, solvents, binders, fillers, aromatic amines, especially primary aromatic amines (PAA), and polycyclic aromatic hydrocarbons (PAH). Hence, the fluid may comprise one or more functional components (active ingredients). For instance, the fluid may comprise a (dissolved) pharmaceutical and/or a (dissolved) nutraceutical, such as for use in the treatment of a disease. Herein, the term "pharmaceutical" may refer to one or more of a drug, a diagnostic marker (such as for MRI), etc. The term "nutraceutical" may amongst others refer to a nutrient, a dietary supplement, a herbal product, etc. The term nutraceutical may especially refer to a food product also having a pharmaceutical function.

The injection of the second liquid jet may affect a property of the material. Hence, in embodiments, the injection method may comprise a second characterization stage comprising determining the property of the target area of the material using the method of the invention. The second characterization stage may especially be temporally arranged subsequent to the injection stage.

The second characterization stage may especially facilitate comparing the property of the material before and after the injection. For instance, the comparison may facilitate determining the effect of an injection on the material, which may inform the future selection of the second jet property, and may provide further information on the material. Further, the second characterization may facilitate determining that the second jet has indeed penetrated the (target area of the) material.

In a further aspect, the invention may provide a system for determining a property of a target area of a material, wherein the system comprises one or more of a microfluidic device for jet ejection, a sensor system, and a control system. Especially, the microfluidic device may be configured to provide a liquid jet to the target area with a jet velocity selected from the range of 2-150 m/s. In embodiments, the sensor system may be configured to detect a deformation of the material in the target area, and especially to provide a related signal to the control system. The control system may especially be configured to determine the property of the target area based on the related signal.

Hence, the system may especially be configured to execute the method of the invention.

In specific embodiments, the system comprises a microfluidic device for jet ejection, a sensor system, and a control system, wherein the microfluidic device is configured to provide a liquid jet to the target area with a jet velocity selected from the range of 2-150 m/s; the sensor system is configured to detect a deformation of the material in the target area and to provide a related signal to the control system; and the control system is configured to determine the property of the target area based on the related signal.

Hence, the system may comprise one or more of a microfluidic device, a sensor system, and a control system. In particular, the control system may be configured to control the microfluidic device and/or the sensor system.

The term "controlling" and similar terms herein may especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system. The control system and the element may thus at least temporarily, or permanently, functionally be coupled. The element may comprise the control system. In embodiments, the control system and the element may not be physically coupled. Control can be done via wired and/or wireless control. The term "control system" may also refer to a plurality of different control systems, which especially are functionally coupled, and of which e.g. one master control system may be a control system and one or more others may be slave control systems.

Microfluidic devices (also "microfluidic platforms" or "microfluidic systems") comprise a broad range of devices related to the field of microfluidics. The field of microfluidics may deal with the behavior, control and manipulation of fluids, typically in small volumes, such as volumes on the order of μL, nL, pL, and fL. Microfluidic devices may be able to precisely control and manipulate fluids on a micrometer-size down to a sub-micrometer-size scale. The channels or features present on a chip may be obtained through a process comprising lithography, dry etching, wet etching, soft-lithography and/or bonding, but may also be provided with other (new) techniques such as laser ablation. With regards to the system of the invention, the microfluidic device may especially be configured for (liquid) jet ejection.

In embodiments, the microfluidic device may be configured to provide a liquid jet to the target area, especially with a jet velocity selected from the range of 1-250 m/s, such as from the range of 2-150 m/s, especially from the range of 5-70 m/s.

In further embodiments, the microfluidic device may be configured to provide the liquid jet with a circular equivalent diameter selected from the range of 30 μm-3 mm.

In further embodiments, the microfluidic device may be configured to provide the liquid jet with a spherical equivalent diameter selected from the range of 30 μm-3 mm.

In further embodiments, the microfluidic device may be configured to provide the liquid jet to the target area at a (jet) angle of 45°-90° (to the target area), such as at an angle of 60-90°, especially at an angle of 75-90°, such as at an angle of 85-90°, especially (essentially) 90°. Similarly, in embodiments, the microfluidic device may be configured to provide the liquid jet to the target area at an angle of 30°-85° (to the target area), such as at an angle of 45-80°, especially at an angle of 50-75°.

The sensor system may especially be configured to sense (or "detect") a signal, such as an optical or acoustic signal. In embodiments, the sensor system may comprise one or more sensors configured to receive one or more signals. For instance, in embodiments, the sensor system may comprise a (high speed) camera configured to detect an optical signal. In further embodiments, the sensor system may comprise a microphone configured to detect an acoustic signal. Hence, in embodiments, the sensor system may be configured to detect optical and/or acoustic radiation, especially optical radiation, or especially acoustic radiation.

In embodiments, the sensor system may be configured to detect a deformation, such as a surface wave, of the material in the target area, and especially to provide a related signal to the control system.

In embodiments, the control system may be configured to determine the property of the target area based on the related signal, such as based on the (detected) deformation, or such as based on the wave property.

The system, especially the control system, may have an operational mode. The term "operational mode" may also be indicated as "controlling mode". The system, or apparatus, or device (see further also below) may execute an action in a "mode" or "operational mode" or "mode of operation". Likewise, in a method an action, stage, or step may be executed in a "mode" or "operation mode" or "mode of operation". This does not exclude that the system, or apparatus, or device may also be adapted for providing another operational mode, or a plurality of other operational modes. Likewise, this does not exclude that before executing the mode and/or after executing the mode one or more other modes may be executed. However, in embodiments a control system (see further also below) may be available, that is adapted to provide at least the operational mode. Would other modes be available, the choice of such modes may especially be executed via a user interface, though other options, like executing a mode in dependence of a sensor signal or a (time) scheme, may also be possible. The operational mode may in embodiments also refer to a system, or apparatus, or device, that can only operate in a single operation mode (i.e. "on", without further tunability).

In embodiments, the operational mode may comprise one or more of an exposure stage, a measurement stage, and an analysis stage.

In the exposure stage, the microfluidic device may (be configured to) provide the liquid jet to the target area.

In the measurement stage, the sensor system may (be configured to) detect a deformation in the target area, and especially to provide a related signal to the control system. In further embodiments, the sensor system may (be configured to) detect the radiation, such as the optical and/or acoustic radiation, from the target area, and especially to provide a related signal to the control system.

In the analysis stage, the control system may (be configured to) determine the property of the target area based on the related signal.

In embodiments, the system may further comprise a contact element. The contact element may be configured to contact the material, especially at a predetermined distance from the target area. In further embodiments, the predetermined distance may be selected from the range of 0-10 mm, such as from the range of 1-7 mm, especially from the range of 2-5 mm.

In further embodiments, the contact element may be configured to arrange the microfluidic device at a distance ≤50 cm from the target area, such as ≤20 cm, especially ≤10 cm (relative from a position at the microfluidic device where the liquid jet leaves the microfluidic device). In further embodiments, the contact element may be configured to arrange the microfluidic device at a distance ≤5 cm from the target area, especially ≤3, such as ≤2 cm. In further embodiments, the contact element may be configured to arrange the microfluidic device at a distance ≥1 cm from the target area, such as ≥3 cm, especially ≥5 cm.

In embodiments, the contact element may especially be detachable. Hence, the system may be configured for functionally coupling to a detachable contact element. Such embodiments may be particularly suitable for conditions where contact with the material is subject to hygiene considerations. In further embodiments, the contact element may be a disposable contact element.

The contact element may further facilitate accessing a target area to be measured which is limited by geometrical constraints.

As described above, in embodiments the material may comprise skin. Hence, in embodiments, the contact element may especially be configured for contacting the skin of a subject.

In further embodiments, the material may comprise an eye. Hence, in embodiments, the contact element may especially be configured for contacting the eye of a subject.

Further, the contact element may be configured to define a chamber (together) with the material, i.e., the contact element and the material may together define a chamber. In embodiments, when the contact element is arranged on the material, the material may thus define at least part of a chamber wall. Especially, the target area may define at least part of a chamber wall. The provision of a chamber may especially facilitate providing controlled conditions at the target area, such as by limiting ambient influence. In further embodiments, the system, especially the control system, may thus be configured to control one or more of a temperature, a (pre-) tension, and a humidity in the chamber. The term "pre-tension" may herein especially refer to providing a tension to the material, especially to the target area, prior to the exposure stage.

Hence, in embodiments, the system may comprise one or more of a temperature control element, a tension providing element, and a humidity control element, such as a humidifier or dehumidifier.

The contact element may especially comprise the tension providing element, i.e., the contact element may, for instance, be configured to stretch the material when arranged on the material.

In embodiments, the system may further comprise a radiation source. The radiation source may especially be configured to provide radiation to the sensor system via the target area, especially during the measurement stage. In particular, the radiation source may be configured to provide the radiation to the target area, for instance when the contact element is arranged on the material, such that reflected radiation is provided from the target area to the sensor system.

It may, however, also be preferable not to contact the material with a contact element, for instance for particularly sensitive materials. Hence, in embodiments, the system may be configured for being arranged remote from the material during operation.

In further embodiments, the radiation source may be configured to provide optical and/or acoustic radiation, especially optical radiation, or especially acoustic radiation.

The system may further comprise a mark projector configured to project a mark, such as a 2D grid, onto the target area, especially during the measurement stage.

In embodiments, the control system may especially be configured to control one or more of the temperature control element, the tension providing element, the humidity control element, the radiation source, and the mark projector.

The system may be part of or may be applied in e.g. (handheld) medical devices, (handheld) cosmetic devices, assembly lines, (3D) printers, robots, sensing applications where the jet is splashed against a surface, say the skin, to obtain reproducible splashing against a sensor surface, modification of coatings or films in industrial settings.

Hence, in embodiments, the system may especially be integrated in a handheld device.

The embodiments described herein are not limited to a single aspect of the invention. For example, an embodiment describing the method may, for example, further relate to the system, especially to an operational mode of the system, or especially to the control system. Similarly, an embodiment of the system describing an operation of the system may further relate to embodiments of the method. In particular, an embodiment of the method describing an operation (of the system) may indicate that the system may, in embodiments, be configured for and/or be suitable for the operation. Similarly, an embodiment of the system describing actions of (a stage in) an operational mode may indicate that the method may, in embodiments, comprise those actions.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 3A-D and FIGS. 4A-F depict measurements obtained with embodiments of the method of the invention.

DETAILED DESCRIPTION OF THE EMBODIMENTS

Figures 1, 2:
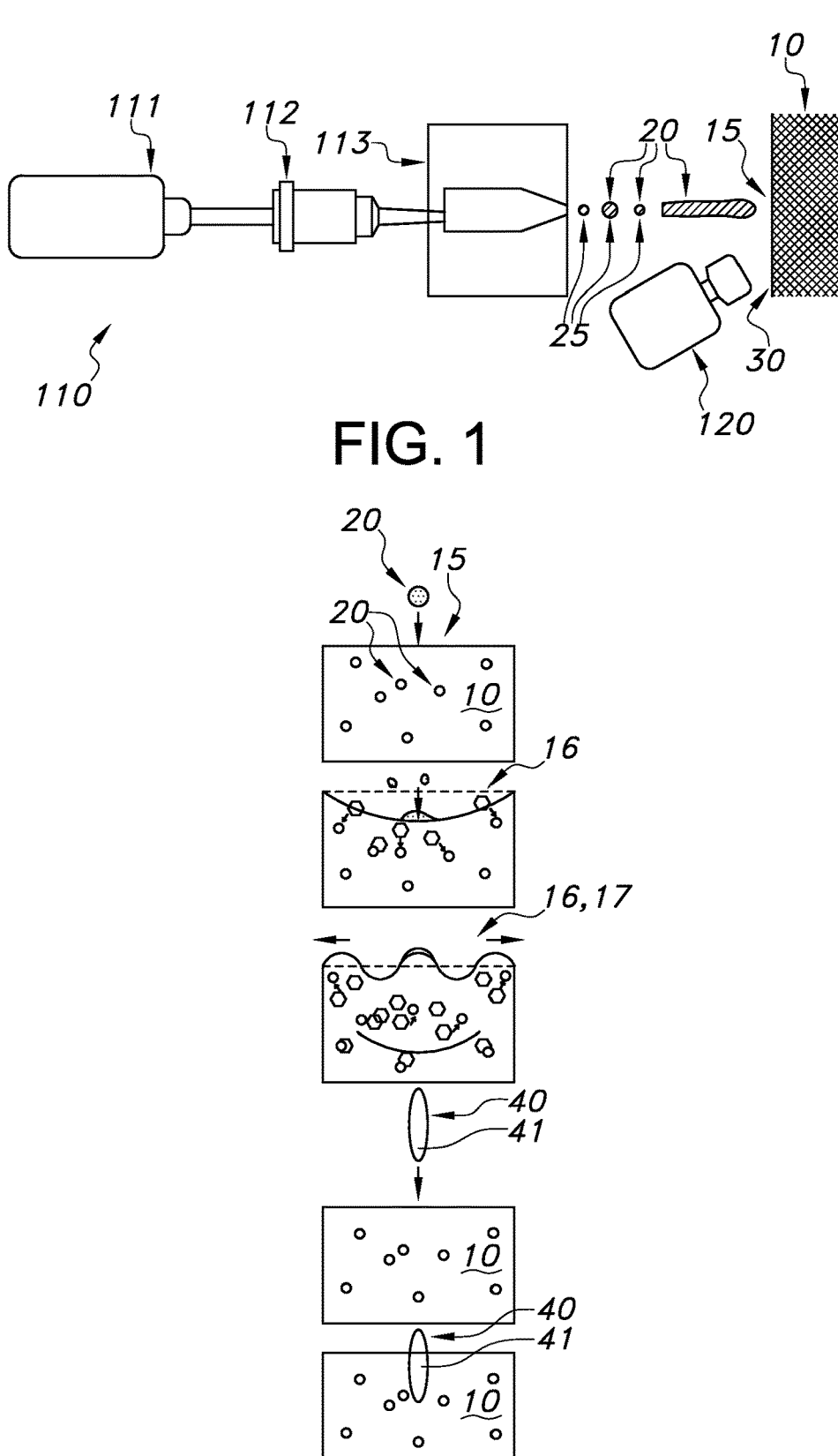
FIGS. 1-2 schematically depict embodiments of the method of the invention.

FIG. 1 schematically depicts an embodiment of the (characterization) method for determining a property of a target area 15 of a material 10, especially a property selected from the group comprising a Young's modulus, a viscous modulus, a shear elasticity, and a shear viscosity. The target area 15 may especially have a size selected from the range of 100 $\mu m^2$-100 $mm^2$. In embodiments, the method may comprise an exposure stage, a measurement stage, and an analysis stage. The exposure stage may comprise providing a liquid jet 20 to the target area 15, especially wherein the liquid jet 20 has a jet velocity selected from the range of 2-150 m/s, such as from the range of 5-70 m/s. The measurement stage may comprise detecting a (spatiotemporal) deformation 16 of the material in the target area 15, and especially providing a related signal. The analysis stage may comprise determining the property of the target area 15 based on the deformation 16, especially based on the related signal.

Specifically, FIG. 1 schematically depicts an experimental setup, wherein thermocavitation is obtained focusing a continuous wave laser at the bottom of a microfluidic device with a microscope objective. The thermocavitated bubble expands and creates a liquid jet that is directed to the material 10 and the material 10 deforms upon the impact. The process is recorded with a high-speed camera with illumination coming from a light source that is reflected on the material surface. High-speed jets may be generated from a thermocavitation process and directed to impact a pendant droplet of different liquids with varying properties. Thermocavitation may refer to the phenomena where a liquid is vaporized locally by means of a focused laser, leading to bubble nucleation. The expansion of the nucleated bubble can be controlled on a microfluidic chip to generate a jet through a flow-focusing effect. Furthermore, the system can be tailored to shoot several continuous jets, which can be used to do a frequency sweep. Jet properties, such as the jet velocity and the jet diameter, can be controlled by varying the laser spot size, power and chip geometry.

Hence, in the depicted embodiment, the liquid jet 20 may be provided with a microfluidic device 110. The microfluidic device may, for instance, comprise a heating source 111, such as a continuous wave laser source, an objective 112, and a microfluidic chip 113. For instance, in embodiments, a liquid in the microfluidic chip 113 may be brought to a boil with the heating source 111 such that a liquid jet 20 is ejected from the microfluidic chip 113. During operation of the microfluidic device 110, laser radiation may be applied to (liquid in the) the microfluidic chip such that the liquid is brought to a boil, resulting in the creation of a fast-expanding bubble. The expansion of the bubble is a conversion of at least part of the laser radiation energy into kinetic energy that is transferred to the liquid that is set in motion. Especially, the microfluidic device may be configured such that the fast-expanding bubble moves towards an opening directed to the target area 15 and thereby transfers kinetic energy to the liquid, which results in the formation of a liquid jet 20 ejected from the opening.

In the depicted embodiment, the liquid jet may be provided at an angle of about 90° to the target area, i.e., the liquid jet may be provided (essentially) perpendicularly to the target area. In further embodiments, the exposure stage may comprise providing the liquid jet 20 to the target area 15 at an angle selected from the range of 45°-90°, such as from the range of 50°-80°.

In embodiments, the exposure stage may comprise varying a jet property of the liquid jet 20, such as by varying the jet velocity in the range of 5-70 m/s, or such as by varying the (spherical equivalent or circular equivalent) diameter of the liquid jet 20 in the range of 30 $\mu m$-3 mm.

In the depicted embodiment, the liquid jet 20 comprises a plurality of (successively provided) droplets 25. The exposure stage may especially comprise providing the plurality of droplets 25 at intervals (independently) selected from the range of 0.02-10 ms. For instance, in embodiments, the plurality of liquid jets 20 may be provided at a frequency selected from the range of 0.001-50 kHz, such as from the range of 0.1-50 KHz.

In further embodiments, the exposure stage may comprise varying a jet property of the liquid jet 20 between (successively provided) droplets 25. In particular, in embodiments, the exposure stage may comprise a first phase and a second phase, wherein (droplets 25 in) the first phase and (droplets 25 in) the second phase differ in one or more of jet velocity, jet intervals, and jet diameter.

In further embodiments, the exposure stage may comprise varying the intervals between two or more successive droplets 25 of the plurality of droplets 25. Especially, the exposure stage may comprise varying the intervals between the plurality of droplets to provide a frequency sweep in the range of 0.1-50 KHz.

In the depicted embodiment, the method, especially the measurement stage, may comprise detecting the deformation 16 following impact with the liquid jet 20 with a sensor system 120, such as with a (high speed) optical camera, or such as with a microphone. In particular, in embodiments, the measurement stage may comprise acoustically detecting the deformation 16 in the target area 15, i.e., the measurement stage may comprise detecting acoustic radiation from the target area 15, and especially providing a related signal.

In embodiments, the method may further comprise a preparation stage. The preparation stage may comprise providing an additive 30 to the target area 15, especially wherein the additive 30 comprises one or more of water and oil. For instance, in embodiments, the preparation stage may comprise spraying the additive (on) to the target area 15.

FIG. 2 schematically depicts a deformation 16 of the target area 15 of the material 10 following an impact of a liquid jet 20. In particular, FIG. 2 schematically depicts a material 10 comprising visible particles 11, wherein the impact of the liquid jet 20 results in a (visible) displacement of the particles 11, as well as in the generation of a surface wave 17 at the target area 15 of the material 10. In particular, both the (extent of) displacement of the particles 11 and the properties of the surface wave 17, such as amplitude and decay rate, may depend on the (viscoelastic) property of the material 10. Hence, the displacement of the particles 11 and the properties of the surface wave may be indicative of the (viscoelastic) property.

FIG. 2 further schematically depicts an embodiment of the injection method for injecting a fluid 41 into a material 10. In particular, the injection method may comprise a characterization stage, a parameterization stage, and an injection stage. The characterization stage (the top three panels) may comprise determining a (viscoelastic) property of a target area 15 of the material 10 using the (characterization) method according to the invention. The parameterization stage may comprise selecting a second jet property for injecting the fluid 41 into the material 10 based on the property (of the material 10), especially wherein the jet property is selected from the group comprising a jet speed, a jet volume, a jet (ejection) rate, and a jet angle. The injection stage may comprise ejecting a second liquid jet 40 towards (the target area 15 of) the material 10 based on the jet property, especially wherein the second liquid jet 40 has the jet property, and especially wherein the second liquid jet 40 comprises the fluid 41.

In general, the injection method may comprise detecting the property of the target area 15 by exposing the target area 15 to the liquid jet 20, and subsequently providing the second liquid jet 40 to inject the fluid 41 at the target area 15. However, for instance for (relatively) homogeneous materials, the injection method may comprise determining a property of the material 10 at a first target area during the characterization stage, and injecting the second liquid jet in the material 10 at a second target area, arranged remotely from the first target area. FIG. 3A-D schematically depicts experimental observations obtained with the embodiment of the method of the invention depicted in FIG. 1. Specifically, processes of bubble generation, jet ejection and impact on the liquid droplet were recorded with a sensor system 120, especially a Photron Fastcam SAX coupled with a 2× microscope objective. A typical experiment duration was ~5 ms and the camera resolution was set to 768×328 pixels at a sample rate of 50 k frames per second with an exposure time of 2.5 μs. Typical images obtained from the experiments are shown in FIG. 3A-D, where one observes how an agarose gel (0.25 wt % agarose) responds to the impact of the liquid jet 20. As can be seen in FIG. 1, the sensor system 120 is arranged at an angle to the target area 15.

The impact of the liquid jet 20 on the target area 15 of the material 10 may result in a surface wave 17 travelling along the target area (also see FIG. 2, FIG. 3A-D). In embodiments, the measurement stage may comprise measuring a wave property of a surface wave 17 (following impact of the liquid jet 20 on the material 10) in the target area 15, wherein the wave property is selected from the group comprising a propagation velocity and an amplitude decay, and wherein the analysis stage comprises determining the (viscoelastic) property based on the wave property.

Figure 3A:
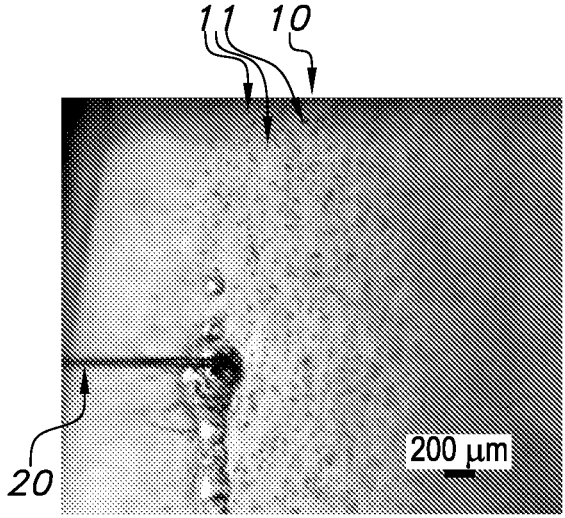
Figure 3B:
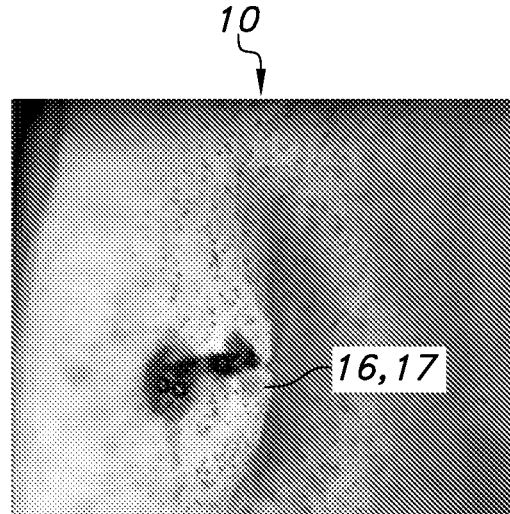
Figure 3C:
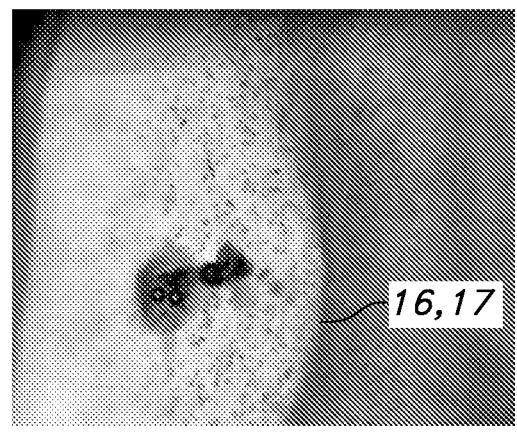
Figure 3D:
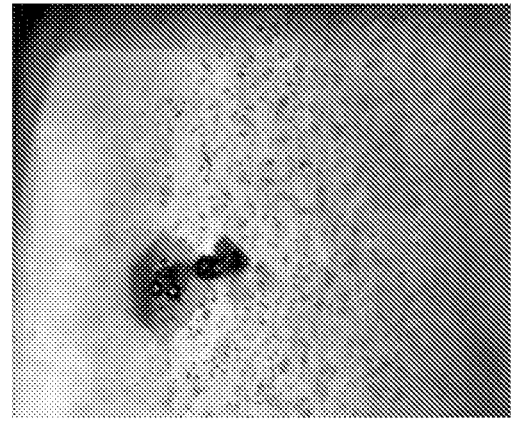

Specifically, FIG. 3A-D correspond to a time series, wherein FIG. 3A corresponds to t=0 (moment of impact), FIG. 3B corresponds to t=1.04 ms, FIG. 3C corresponds to t=1.68 ms, and FIG. 3D corresponds to t=3.68 ms.

In particular, FIG. 3A-D demonstrate that a surface wave 17 is generated (and observed) following the impact of the liquid jet 20 on the material 10.

FIG. 4A-F schematically depict experimental observations for the same experiments as in FIG. 3A-D, but with the sensor system 120 arranged perpendicular to (the axis of) impact of the liquid jet 20. As the material 10, here especially an agarose gel, comprises visible particles 11, the displacement of the particles 11 and thus the displacement of the material 10 can be observed. In particular, FIG. 4A-C indicate the observed horizontal displacement (in agarose 0.5 wt %), i.e., the left-right displacement in-plane of the image. FIG. 4D-F indicate the observed vertical displacement (in agarose 0.5 wt %), i.e., the top-down displacement in-plane of the image. Further, FIG. 4A,D correspond to t=0.06 ms, FIG. 4B,E correspond to t=0.2 ms, and FIG. 4C,F correspond to t=0.4 ms. From the displacements the stress of the gel at each point can be calculated.

Table 1 indicates the measured properties of aqueous agarose gels based on the observations (see formulae above), including determined surface wave speeds, in triplicates:

| Material | Young's Modulus (Pa) | Shear elasticity (Pa) | Shear viscosity (Pa s) |
|---|---|---|---|
| Agarose 0.25 wt. % | 2264 | 755 | 0.144 |
| | 1400 | 467 | 0.092 |
| | 2537 | 846 | 0.161 |
| Agarose 0.5 wt. % | 5368 | 1789 | 0.330 |
| | 4971 | 1657 | 0.307 |
| | 5569 | 1856 | 0.343 |

Figure 5:
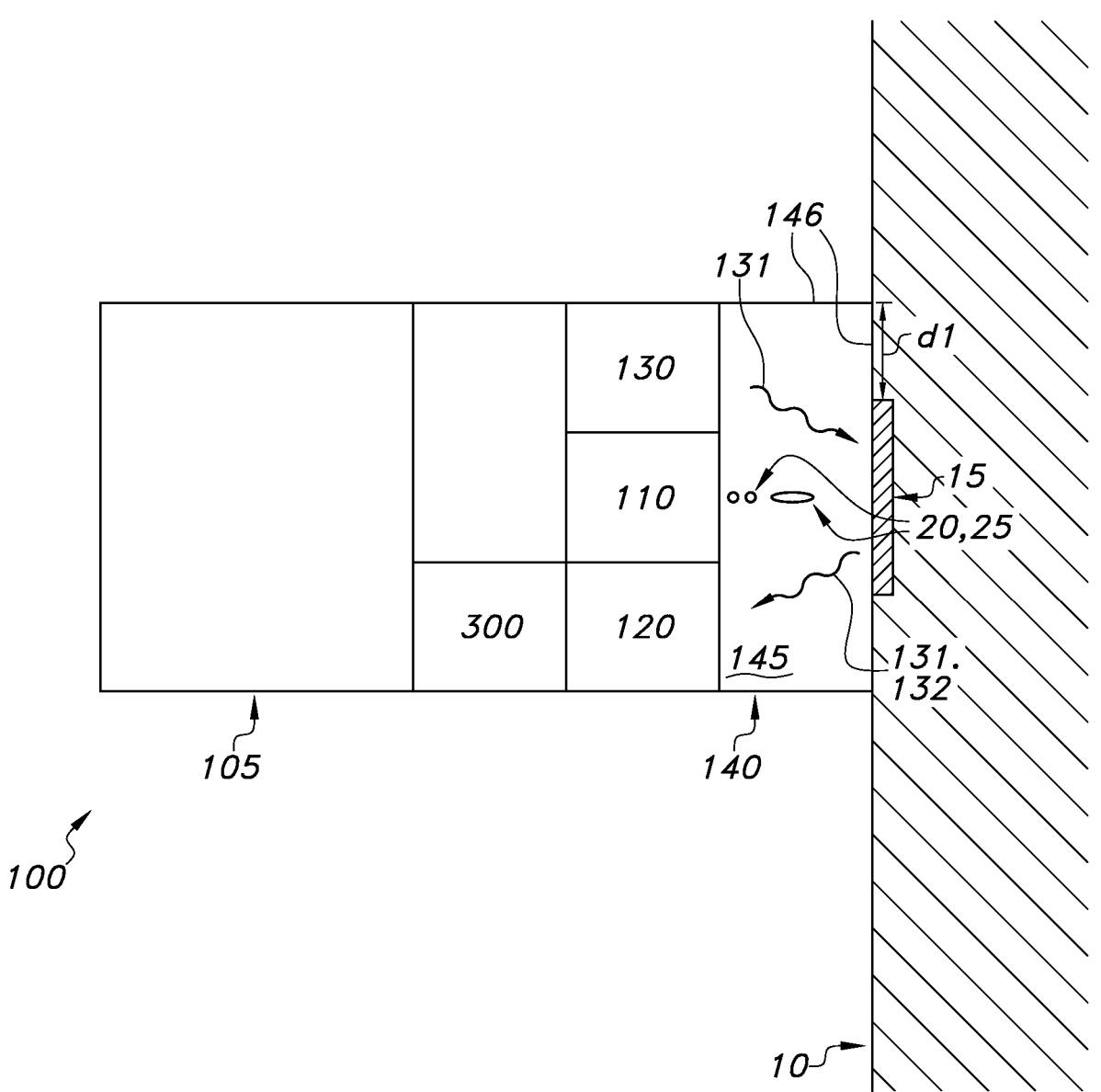
FIG. 5 schematically depicts an embodiment of the system of the invention.

FIG. 5 schematically depicts an embodiment of the system for determining a property of a target area 15 of a material 10. In the depicted embodiment, the system 100 comprises a microfluidic device 110 for jet ejection, a sensor system 120, and a control system 300. The microfluidic device 110 may be configured to provide a liquid jet 20 to the target area 15, especially with a jet velocity selected from the range of 2-150 m/s, such as from the range of 5-70 m/s. The sensor system 120 may be configured to detect a deformation 16 (see FIG. 4) of the material 10 in the target area 15 and to provide a related signal to the control system 300. The control system 300 may be configured to determine the property of the target area 15 based on the related signal.

In the depicted embodiment, the system 100 further comprises a contact element 140, wherein the contact element 140 is configured to contact the material 10 at a predetermined distance d1 from the target area, especially wherein the predetermined distance d1 is selected from the range of 0-10 mm.

In specific embodiments, the contact element 140 may be configured for contacting a skin of a subject.

In particular, the contact element 140 may be configured to define a chamber 145 with the material 10, especially wherein the target area 15 defines at least part of a chamber wall 146. Providing a chamber 145 around the target area 15 may facilitate providing controlled conditions at the target area, which may reduce measurement noise, reduce liquid splashing, and may facilitate determining the property at different ambient conditions. Hence, in embodiments, the system 100 may be configured to control one or more of a temperature, a (pre-) tension, and a humidity in the chamber 145.

Hence, in embodiments, the system 100 may especially comprise a temperature control element configured to control a temperature in the chamber 145.

In further embodiments, the system 100 may comprise a tension providing element configured to provide a tension on the target area 15. Especially, the contact element 140 may comprise the tension providing element.

In further embodiments, the system 100 may comprise a humidity control element, such as a humidifier and/or a dehumidifier, configured to control a humidity in the chamber 145.

In the depicted embodiment, the system 100 further comprises a radiation source 130. The radiation source 130 may be configured to provide (measurement) radiation 131, especially optical radiation, or especially acoustic radiation, to the sensor system 120 via the target area 15. Hence, the radiation source 130 may be configured to provide the radiation 131 to the target area 15 such that reflected radiation 131, 132 reaches the sensor system 120.

Hence, the sensor system 120 may especially be configured to detect the (measurement) radiation 131, such as the reflected radiation 132. In particular, in embodiments, the sensor system 120 may be configured to detect optical radiation. In further embodiments, the sensor system 120 may be configured to detect acoustic radiation.

In further embodiments, the sensor system 120 may be configured to detect ambient radiation reflected at the target area. Hence, in embodiments, the system 100 may be devoid of a radiation source 130.

In embodiments, the system 100, especially the control system 300, may have an operational mode. The operational mode may especially comprise an exposure stage, a measurement stage, and an analysis stage. In the exposure stage, the microfluidic device may (be configured to) provide the liquid jet 20 to the target area 15. In the measurement stage, the sensor system 120 may (be configured to) detect the radiation from the target area 15, and especially (to) provide the related signal to the control system 300. In the analysis stage, the control system 300 may determine the property of the target area 15 based on the related signal.

In the depicted embodiment, the system 100 may especially be integrated in a handheld device 105.

FIG. 5 further schematically depicts an embodiment of the method, wherein the measurement stage comprises (i) providing (measurement) radiation 131, especially laser (measurement) radiation 131, to the target area 15, and (ii) detecting reflected (measurement) radiation 131 from the target area 15, and especially providing a related signal. In such embodiments, the analysis stage may especially comprise determining the property of the target area 15 based on the reflected radiation 131, such as based on the related signal.

Figure 6:
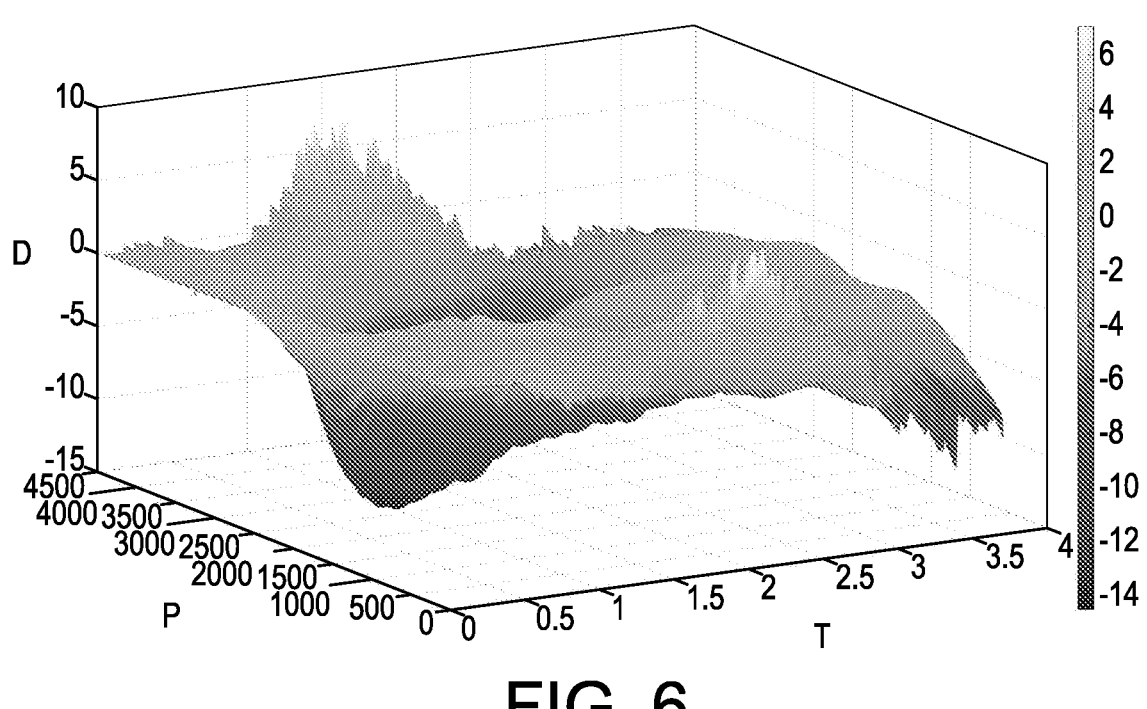
FIGS. 6-7 schematically depict experimental results. The schematic drawings are not necessarily on scale.
Figure 7:
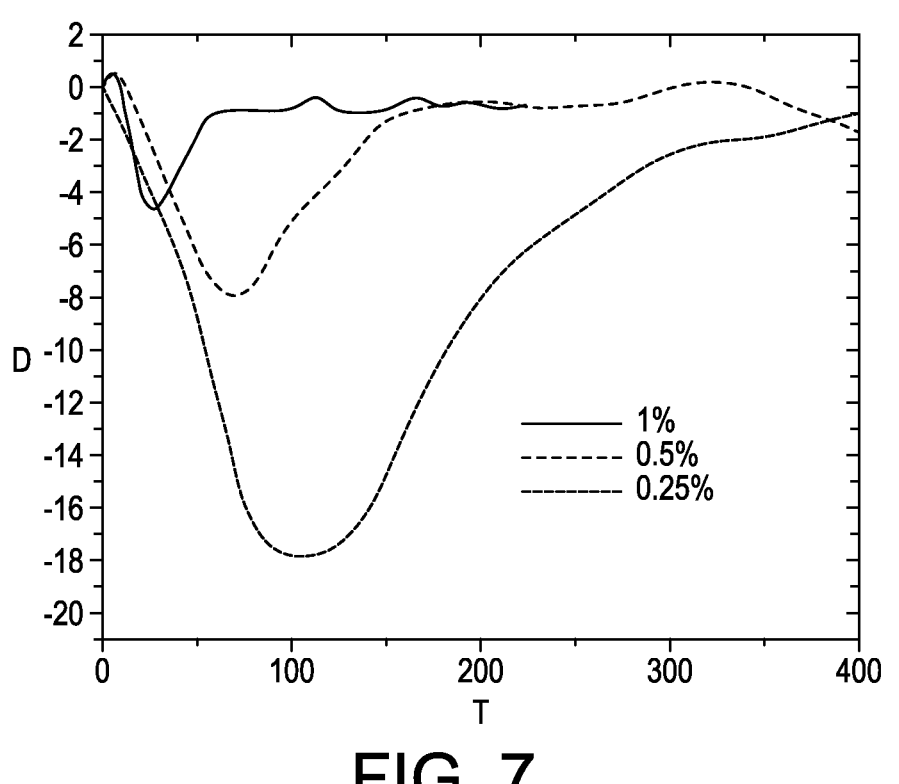

FIG. 6-7 schematically depict experimental results obtained using the system and the method of the invention. In particular, a liquid jet 20 was ejected onto a target area 15 of a material 10, specifically an agarose substrate, resulting in a deformation of the material 10.

FIG. 6 schematically depicts the deformation D (μm) of the agarose substrate as a function of time T (ms) and position P (μm). The vertical axis depicted in the figure indicates the deformation in the agarose substrate (also indicated by the greyscale colorbar). From the depicted 3D plot, the deformation at specific times or locations may be determined for further analysis (see also FIG. 7). Especially, from the impact on different substrates the deformation for each position in the agarose can be tracked in time.

FIG. 7 depicts the deformation at the impact center of different agarose substrates when impacted by a liquid jet 20, especially at a jet velocity of 33 m/s. The vertical axis indicates the deformation D (pixels) of the substrate and the horizontal axis indicates time T (frames). The deformation of three different agarose substrates is depicted, corresponding to agarose concentrations of 0.25 wt. %, 0.5 wt. % and 1 wt. %. In the figure the difference in response time between the different agarose concentrations can be observed. The maximum deformation is larger for lower concentrations of agarose. Furthermore, the substrate undergoes maximum deformation (and recovers therefrom) sooner for higher agarose concentrations. Hence, the deformation may be informative on the property of the material at the target area.

The term "plurality" refers to two or more. Furthermore, the terms "a plurality of" and "a number of" may be used interchangeably.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%. Moreover, the terms "about" and "approximately" may also relate to 90% or higher, such as 95% or higher, especially 99% or higher, even more especially 99.5% or higher, including 100%. For numerical values it is to be understood that the terms "substantially", "essentially", "about", and "approximately" may also relate to the range of 90%-110%, such as 95%-105%, especially 99%-101% of the values(s) it refers to.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The devices, apparatus, or systems may herein amongst others be described during operation. As will be clear to the person skilled in the art, the invention is not limited to methods of operation, or devices, apparatus, or systems in operation.

The term "further embodiment" and similar terms may refer to an embodiment comprising the features of the previously discussed embodiment, but may also refer to an alternative embodiment.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", "include", "including", "contain", "containing" and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings. Moreover, if a method or an embodiment of the method is described being executed in a device, apparatus, or system, it will be understood that the device, apparatus, or system is suitable for or configured for (executing) the method or the embodiment of the method, respectively.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A method for determining a property of a target area of a material, wherein the target area has a size selected from a range of 100 μm²-100 mm², wherein the method comprises:

an exposure stage comprising providing a liquid jet to the target area, wherein the liquid jet has a jet volume selected from a range of ≤500 nL, wherein the liquid jet has a jet velocity selected from a range of 2-150 m/s, wherein the jet velocity is selected to be sufficient to provide a deformation in the material, wherein the deformation comprises a surface wave, and wherein the jet velocity is selected to be below a threshold for injection into the material;

a measurement stage comprising detecting radiation from the target area, and comprising measuring a wave property of the surface wave in the target area and providing a related signal, wherein the wave property is selected from the group comprising a propagation velocity and an amplitude decay, wherein the related signal is a signal related to the wave property of the surface wave; and an analysis stage comprising determining the property of the target area based on the wave property.

2. The method according to claim 1, wherein the liquid jet has a jet velocity selected from a range of 5-70 m/s, wherein the liquid jet has a circularly equivalent diameter selected from a range of 30 μm-3 mm, and wherein the exposure stage comprises providing the liquid jet to the target area at an angle of 45°-90°.

3. The method according to claim 2, wherein the exposure stage comprises varying the jet velocity in a range of 5-70 m/s.

4. The method according to claim 2, wherein the exposure stage comprises varying the circularly equivalent diameter of the liquid jet in a range of 30 μm-3 mm.

5. The method according to claim 1, wherein the liquid jet has a jet diameter selected from a range of 25-300 μm.

6. The method according to claim 1, wherein the liquid jet comprises a plurality of droplets, wherein the plurality of droplets are provided at intervals selected from a range of 0.02-10 ms.

7. The method according to claim 6, wherein the exposure stage comprises varying the intervals between two or more successive droplets of the plurality of droplets.

8. The method according to claim 1, wherein the target area has a size selected from a range of 300 μm²-3 mm², wherein the measurement stage comprises projecting a mark on at least part of the target area, and wherein the measurement stage comprises optically detecting the deformation in the target area.

9. The method according to claim 1, wherein the measurement stage comprises acoustically detecting the deformation in the target area.

10. The method according to claim 1, wherein the measurement stage comprises (i) providing radiation to the target area, and (ii) detecting reflected radiation from the target area, wherein the analysis stage comprises determining the property of the target area based on the reflected radiation.

11. The method according to claim 1, wherein the method further comprises a preparation stage, wherein the preparation stage comprises providing an additive to the target area, wherein the additive comprises one or more of water and oil.

12. The method according to claim 1, wherein the property is selected from the group comprising a Young's modulus, a viscous modulus, a shear elasticity, and a shear viscosity.

13. The method according to claim 1, wherein the material comprises ex vivo skin or an ex vivo eye.

14. The method according to claim 1, wherein the material comprises a coating.

15. An injection method for injecting a fluid into a material, wherein the method comprises:

a characterization stage comprising determining the property of the target area of the material using the method according to claim 1;

a parameterization stage comprising selecting a second jet property for injecting the fluid into the material based on the property, wherein the second jet property is selected from the group comprising a jet velocity, a jet volume, a jet rate, and a jet angle; and an injection stage comprising ejecting a second liquid jet based on the second jet property towards the target area to inject the fluid into the material, wherein the second liquid jet comprises the fluid.

16. The injection method according to claim 15, wherein the parameterization stage comprises selecting the second jet property based on the property and a target parameter, wherein the target parameter is selected from the group comprising an injection depth and an injection volume.

17. The method according to claim 1, wherein the measurement stage comprises detecting optical radiation from the target area using a sensor system.

18. A system for determining a property of a target area of a material, wherein the system comprises a microfluidic device for jet ejection, a sensor system, and a control system, wherein:

the microfluidic device is configured to provide a liquid jet to the target area with a jet velocity selected from a range of 2-150 m/s, wherein the liquid jet has a jet volume selected from a range of ≤500 nL, wherein the jet velocity is selected to be sufficient to provide a deformation in the material, wherein the deformation comprises a surface wave, and wherein the jet velocity is selected to be below a threshold for injection into the material;

the sensor system is configured to detect radiation from the target area, and to measure a wave property of the surface wave in the target area and to provide a related signal, wherein the wave property is selected from the group comprising a propagation velocity and an amplitude decay, wherein the related signal is a signal related to the wave property of the surface wave; and the control system is configured to determine the property of the target area based on the wave property.

19. The system according to claim 18, wherein the sensor system is configured to detect optical and/or acoustic radiation, and wherein the system has an operational mode comprising:

an exposure stage comprising the microfluidic device providing the liquid jet to the target area;

a measurement stage comprising the sensor system detecting the optical and/or acoustic radiation from the target area, and providing the related signal to the control system;

an analysis stage comprising the control system determining the property of the target area based on the wave property.

20. The system according to claim 18, wherein the system is integrated in a handheld device.

21. The system according to claim 18, wherein a contact element is configured to define a chamber with the material, wherein the system is configured to control one or more of a temperature, a tension, and a humidity in the chamber.

22. The system according to claim 18, wherein the system comprises a contact element configured for contacting a skin of a subject.

23. The system according to claim 18, wherein the sensor system is configured to detect optical radiation.

24. A method for determining a property of a target area of a material, wherein the target area has a size selected from a range of 100 $\mu m^2$-100 $mm^2$, wherein the method comprises:

an exposure stage comprising ejecting a liquid jet from a microfluidic device to the target area, wherein the liquid jet has a jet volume selected from a range of ≤500 nL, wherein the liquid jet has a jet velocity selected from a range of 2-150 m/s, wherein the jet velocity is selected to be sufficient for impact of the jet on the material to result in a surface wave in the material, and wherein the jet velocity is selected to be below a threshold for injection into the material;

a measurement stage comprising detecting radiation reflected from the target area, and determining a wave property of the surface wave in the target area from the radiation, wherein the wave property is selected from the group comprising a propagation velocity and an amplitude decay; and an analysis stage comprising determining the property of the target area based on the wave property.

25. A system for determining a property of a target area of a material, wherein the system comprises a microfluidic device for jet ejection, a sensor system, and a control system, wherein:

the microfluidic device is configured to provide a liquid jet to the target area with a jet velocity selected from a range of 2-150 m/s, wherein the liquid jet has a jet volume selected from a range of ≤500 nL, wherein the jet velocity is selected to be sufficient to provide a deformation in the material, wherein the deformation comprises a surface wave, and wherein the jet velocity is selected to be below a threshold for injection into the material;

the sensor system is configured to detect radiation from the target area, and to measure a wave property of the surface wave in the target area from the radiation, wherein the wave property is selected from the group comprising a propagation velocity and an amplitude decay; and the control system is configured to determine the property of the target area based on the wave property.

* * * * *